US00PP17596P3

(12) United States Plant Patent
Hasegawa

(10) Patent No.: US PP17,596 P3
(45) Date of Patent: Apr. 17, 2007

(54) CARNATION PLANT NAMED 'CFPC ANNETTE'

(50) Latin Name: *Hybrid Dianthus caryophyllus*
Varietal Denomination: CFPC Annette

(75) Inventor: Oscar T. Hasegawa, Salinas, CA (US)

(73) Assignee: California Florida Plant Company, Salinas, CA (US)

( * ) Notice: Subject to any disclaimer, the term of this patent is extended or adjusted under 35 U.S.C. 154(b) by 52 days.

(21) Appl. No.: 11/177,884

(22) Filed: Jul. 8, 2005

(65) Prior Publication Data

US 2007/0011789 P1 Jan. 11, 2007

(51) Int. Cl.
*A01H 5/00* (2006.01)

(52) U.S. Cl. ..... Plt./276

(58) Field of Classification Search ..... Plt./276
See application file for complete search history.

(56) References Cited

U.S. PATENT DOCUMENTS

PP8,419 P 10/1993 Jessel ..... Plt./70.6

OTHER PUBLICATIONS

2001–2002 California Florida Plant Company brochure listing the variety 'CFPC Cupid'. See, e.g., p. 4 (photograph).
2004–2005 California Florida Plant Company brochure listing the variety 'CFPC Cupid'. See, e.g., p. 4 (photograph).

*Primary Examiner*—Kent Bell
*Assistant Examiner*—Annette H Para
(74) *Attorney, Agent, or Firm*—Winston & Strawn, LLP

(57) ABSTRACT

A new variety of carnation plant named 'CFPC Annette' having large light pink flowers in a spray-type blooming habit.

1 Drawing Sheet

Latin name of the genus and species: Botanical classification: *Dianthus caryophyllus.*

Variety denomination: The new carnation variety denomination is 'CFPC Annette'.

BACKGROUND OF THE INVENTION

The present invention comprises a new and distinct cultivar of hybrid carnation botanically known as *Dianthus caryophyllus,* and referred to by the cultivar name 'CFPC Annette'.

'CFPC Annette', identified as selection no. 020614, originated from a cross made by Roy Stahlhut in a controlled breeding program in Salinas, Calif.

The female parent of the new variety is the unpatented variety known as selection no. 000132 and the male parent is the patented variety known as 'CFPC Cupid' (U.S. Plant Pat. No. 8,419). The new variety 'CFPC Annette' has been asexually reproduced by vegetative side shoot cuttings in Salinas, Calif. and the distinguishing characteristics are retained through successive generations of asexual reproduction.

BRIEF SUMMARY OF THE INVENTION

'CFPC Annette' is a potted spray-type of carnation plant variety having large light pink flowers.

COMPARISON WITH FEMALE PARENT

Plants of the new carnation variety 'CFPC Annette' are similar to the female parent selection no. 000132 in plant habit and growth rate, but differed from plants of the female parent in at least the following characteristic:

1. The new variety 'CFPC Annette' produces large pink flowers while the female parent selection no. 000132 produces large white flowers.

COMPARISON WITH MALE PARENT

Plants of the new carnation variety 'CFPC Annette' are similar to the male parent 'CFPC Cupid' in plant habit and growth rate. In side-by-side comparisons in Salinas, Calif., under commercial practice, plants of the new carnation variety 'CFPC Annette' differed from plants of the male parent 'CFPC Cupid' in the following characteristics:

1. The new variety 'CFPC Annette' produces large light pink flowers whereas the male parent 'CFPC Cupid' produces large flowers that are medium to dark pink.
2. The new variety 'CFPC Annette' produces flowers without splitting of the calyx while the flowers of the male parent 'CFPC Cupid' tend to split the calyx.

BRIEF DESCRIPTION OF ILLUSTRATION

Typical specimens of the plant and flowers for the new carnation variety 'CFPC Annette' are shown in the accompanying photograph. The colors shown are as true as possible within the usual limits of this kind of illustration.

FIG. 1 is a whole plant view of the new variety 'CFPC Annette' grown in a pot. The plant shown in the illustration is 119 days from date of planting.

DETAILED BOTANICAL DESCRIPTION

The following description of the new carnation variety 'CFPC Annette' is of plants 119 days from the date of planting growth in a commercial greenhouse in Salinas, Calif. in the month of December. The cultivar has not been observed under all possible environmental conditions. The phenotype may vary significantly with variations in the environment such as temperature, length of day and light intensity without any variance in genotype.

Plants of the new variety have been grown successfully under temperature conditions averaging about 18° C. at night and about 24° C. to 28° C. during the day under light conditions of about 12 hours. Plants are daylight neutral and flower throughout the year. Chemical growth regulators are not required for production.

The new variety may be produced as a potted spray-type carnation. To produce a commercial product the plants may be pinched once with the center bud removed. Pinched plants are about 16.5 cm tall and about 17.8 cm in diameter. Flower diameter averages about 5.4 cm with a crown of about 1.9 cm. Foliage is generally about 11.4 cm long and about 0.8 cm at the widest point. The typical container size for commercial growth is 4½ inches. It has been observed that the shelf life of the new variety is about 21 days with the first appearance of color in the buds occurring at about 100–110 days after planting of cuttings. The commercial classification of the new carnation variety is a potted spray-type.

The following description is with respect to a plant produced as a potted spray-type. The plant and flower measurements and foliage size are established as an average using standard commercial cultural practices. In the description of this new carnation variety, color values have been taken from The Royal Horticultural Society Colour Chart (R.H.S.C.C.).

PLANT

Height (cm): 16.5.
Form: Herbaceous.
Growing habit: Semi-upright.
Branching characteristics: 2–4 laterals per stem.
Breaking action: Very good; 5–6 breaks per plant with strong straight stems.
First appearance of color in buds: 100–110 days after planting.
Vigor: Excellent.
Shelf life: 21 days.
Blooming habit: Spray type.
Blooming season: Year round.
Lastingness of blooms: About 10 days.
Disease (susceptibility/resistance observed): Good resistance to soil-borne diseases such as *Fusarium oxysporum* and *F. graminearium,* and root rots such as damping off, water molds and similar types, as is typical of carnations.
Pest (susceptibility/resistance observed): None observed.
Drought and temperature (susceptibility/resistance observed): None observed.
Mutation prone: No.
Propagation:
*Type.*—Side shoot cuttings.
*Time to rooting.*—17 days with soil temperatures of 18° C. to 21° C.
*Rooting habit.*—Good fibrous system.
Growth treatments or special conditions: None.

FOLIAGE

Stem:
*Length (cm).*—14.6.
*Diameter (cm).*—Base (cm): 0.5. Apex (cm): 0.3.
*Texture.*—Smooth.
*Cross section.*—Edged.
*Color.*—139D.
Number of leaves per lateral branch: 16–18.
Arrangement of leaves: Bi-lateral along the stem.
*Shape of leaf.*—Long, narrow, lanceolate.
*Size of leaf.*—Width (cm): 0.8. Length (cm): 11.4.
*Leaf apex.*—Acute.
*Edge.*—Smooth.
*Surface texture.*—Top: smooth. Bottom: smooth.
Leaf venation: Prominent mid-vein at underside.
Leaf longitudinal axis: Recurved.
Leaf cross section (upper side): Concave.
Leaf color:
*Mature leaf, upper side.*—137A. Under side: 137B.
*Young leaf, upper side.*—137A. Under side: 137B.
Leaf waxy layer: Weak.

FLOWER

Flower appearance: Matte.
Flower type: Double.
Flower profile of upper part of corolla: Convex.
Flower profile of lower part of corolla: Flat.
Flower shape: Dome shaped, round.
Number of blossoms per branch: 10–11.
*Depth of fully expanded blossoms (cm).*—1.9.
*Diameter of fully expanded blossoms (cm).*—5.4.
Calyx:
*Sepals number.*—5.
*Length (cm).*—0.6.
*Width (cm).*—0.6.
*Color.*—Outer side: tip: 137C base: 138C. Inner side: tip: 138C base: 138D.
*Texture.*—Smooth.
*Appearance.*—Matte.
*Shape.*—Cylindrical.
Flower petals:
*Form shape.*—Fan shaped.
*Petal edge.*—Serrated: Width (mm) <1. Depth (mm): <1. Edge type: crenate-dentate.
*Texture.*—Smooth.
*Appearance.*—Matte.
*Petal surface of blade.*—Flat.
*Number per flower.*—28.
*Outer petals.*—Length (cm): 4.9. Width (cm): 3.0.
*Inner petals.*—Length (cm): 4.1. Width (cm): 2.4.
Fragrance: None to weak sweet.
Flower bud (at onset of color):
*Length (cm).*—2.5.
*Diameter (cm).*—0.9.
*Form/shape.*—Ovoid.
Flower color:
*1. General tonality.*—Light pink.
*2. Petals, upper surface.*—56C.
*3. Petals, lower surface.*—56D.
*4. Petals, edge.*—56C.
*5. Petals, center.*—56B.
*6. Early bud.*—56C.
Petal macule (random spots): Absent.
Flower progression with age: Color remains fairly constant.
Other distinguishing characteristics: Partially opened bud has a unique rose-like appearance.

REPRODUCTIVE ORGANS

Gynoecium: Pistillate.
*Pistil number.*—1.
*Pistil length (cm).*—3.1.
*Pistil color.*—Whiter than 155D.
*Stigma number.*—Only 2.
*Stigma color.*—Very pale pink.
*Stigma shape.*—Filamentous.
*Style color.*—Whiter than 155D.
*Style number.*—Only 2.

Ovary:

*Shape.*—Ovoid.

*Surface.*—Smooth.

*Color.*—Base: 155D. Body: 144A. Apex: 144A.

Androecium: None produced.

Fruit and seeds: None produced.

What is claim is:

1. A new and distinct variety of carnation plant, substantially as described and illustrated herein.

* * * * *

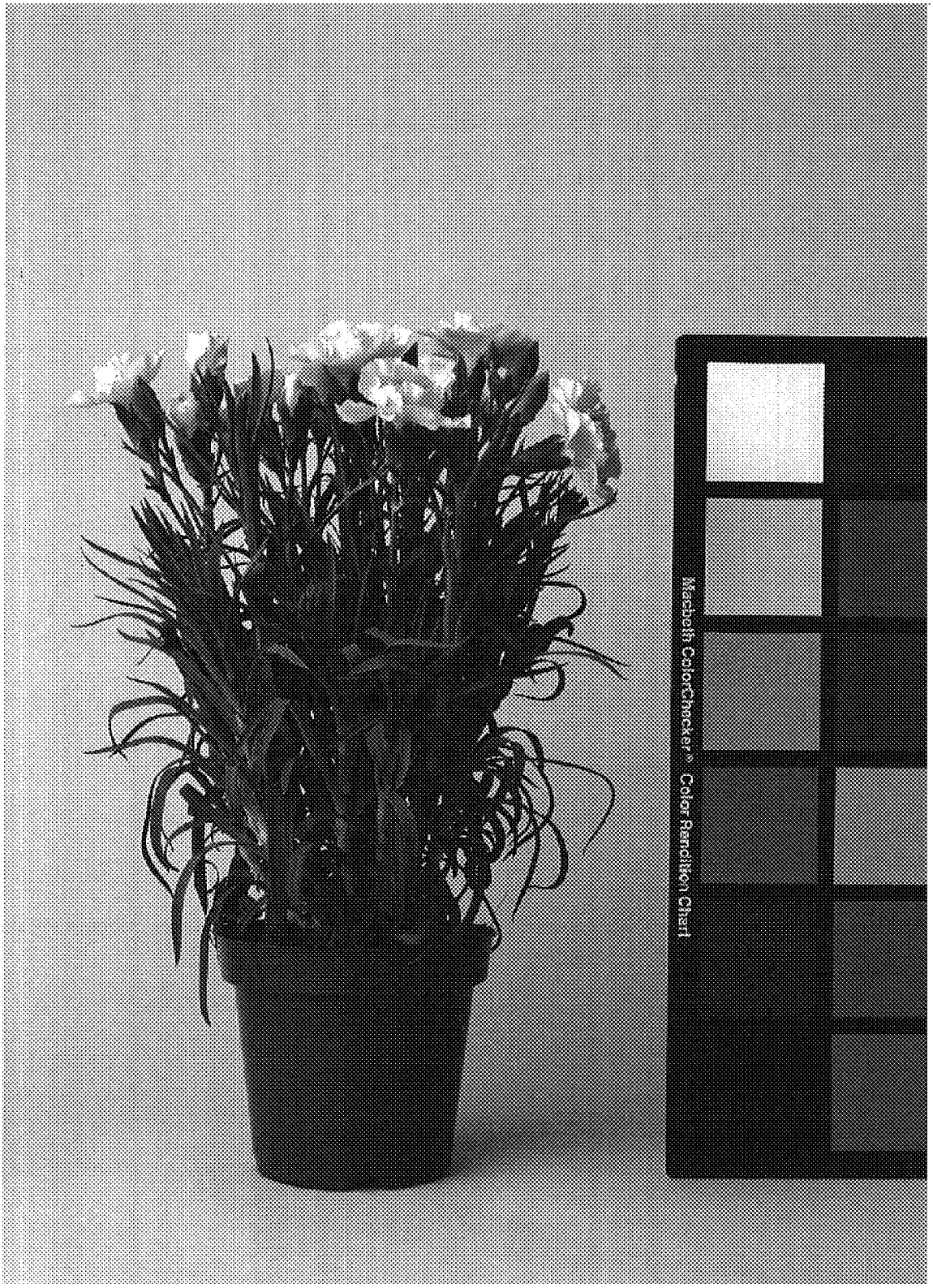
Macbeth ColorChecker® Color Rendition Chart

UNITED STATES PATENT AND TRADEMARK OFFICE

CERTIFICATE OF CORRECTION

PATENT NO. : PP 17,596 P3
APPLICATION NO. : 11/177884
DATED : April 17, 2007
INVENTOR(S) : Oscar T. Hasegawa It is certified that error appears in the above-identified patent and that said Letters Patent is hereby corrected as shown below:

Change the inventor from "Oscar T. Hasegawa, Salinas, CA (US)" to --Roy Stahlhut, Watsonville, CA (US)--.

Signed and Sealed this

Seventh Day of August, 2007

JON W. DUDAS
*Director of the United States Patent and Trademark Office*